United States Patent
Ellman et al.

(12)
(10) Patent No.: US 6,447,510 B1
(45) Date of Patent: *Sep. 10, 2002

(54) MICROLARYNX ELECTROSURGICAL PROBE FOR TREATING TISSUE

(76) Inventors: Alan G. Ellman, 1135 Railroad Ave., Hewlett, NY (US) 11557; Jon C. Garito, 1135 Railroad Ave., Hewlett, NY (US) 11557

( * ) Notice: Subject to any disclaimer, the term of this patent is extended or adjusted under 35 U.S.C. 154(b) by 44 days.

This patent is subject to a terminal disclaimer.

(21) Appl. No.: 09/728,383

(22) Filed: Dec. 4, 2000

(51) Int. Cl.[7] .............................................. A61B 18/18
(52) U.S. Cl. ........................................... 606/45; 606/41
(58) Field of Search ..................... 606/41, 42, 45–50

(56) References Cited

U.S. PATENT DOCUMENTS

| | | | |
|---|---|---|---|
| 4,481,948 A | * 11/1984 | Sole | 219/236 |
| 5,261,906 A | * 11/1993 | Pennino et al. | 606/41 |
| 5,374,188 A | * 12/1994 | Frank et al. | 433/215 |
| 5,505,728 A | 4/1996 | Ellman et al. | |
| 5,536,267 A | * 7/1996 | Edwards et al. | 604/22 |
| 5,571,101 A | * 11/1996 | Ellman et al. | 606/45 |
| D377,524 S | * 1/1997 | Lipp | D24/130 |
| 5,741,250 A | * 4/1998 | Garito et al. | 606/45 |
| 5,957,921 A | * 9/1999 | Mirhashemi et al. | 606/34 |

FOREIGN PATENT DOCUMENTS

WO  WO 97/30646  * 8/1997

* cited by examiner

Primary Examiner—Michael Peffley

(57) ABSTRACT

A unipolar electrosurgical instrument that is configured for use in MIS and other electrosurgical procedures, primarily for the treatment of benign and malignant lesions of the upper aerodigestive tract. The instrument is configured to cooperate with the cannula of a laryngo-pharyngoscopes. The shape includes a short proximal section at an angle to a long middle section which leads to an offset working end containing a unipolar electrode. When energized, a unipolar discharge is generated at the working end of the electrode.

8 Claims, 2 Drawing Sheets

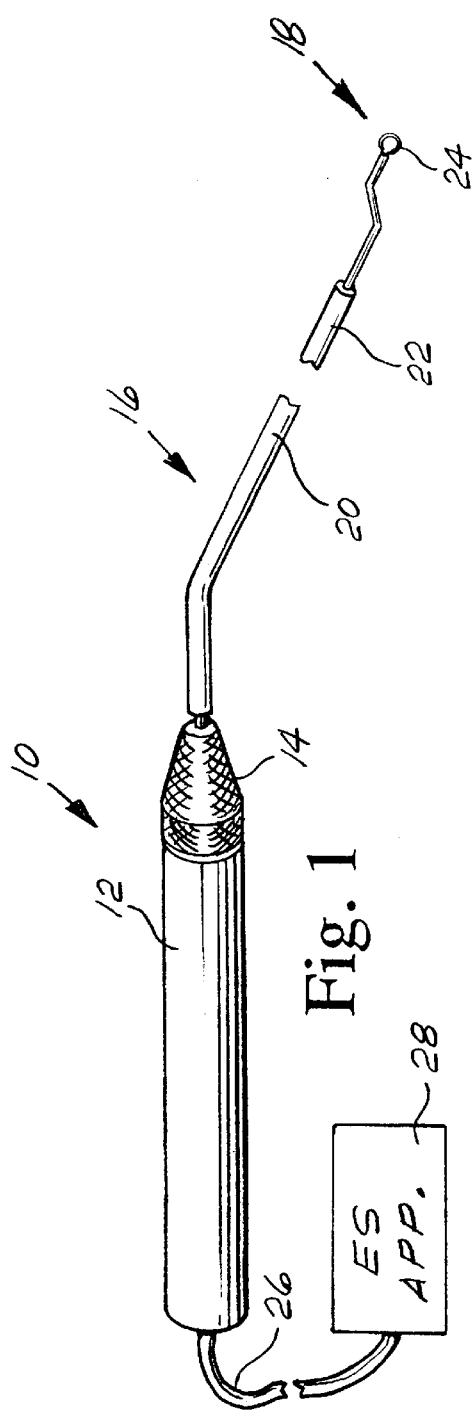
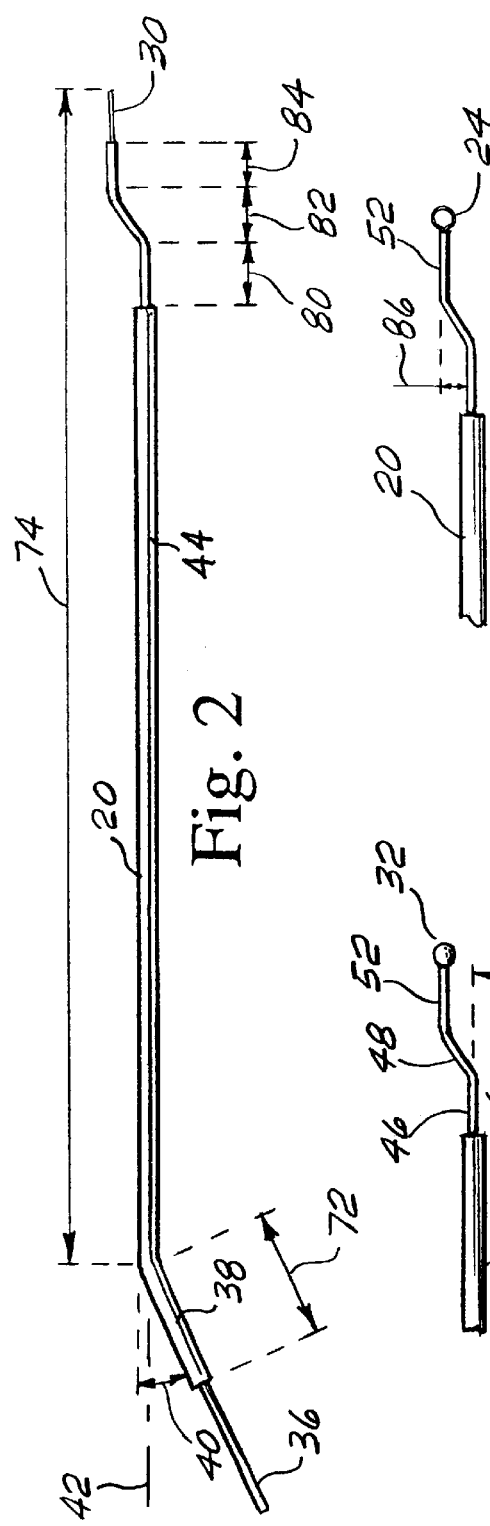

MICROLARYNX ELECTROSURGICAL PROBE FOR TREATING TISSUE

This invention relates to a microlarynx electrosurgical probe for treating ailments or diseases of the larynx.

BACKGROUND OF THE INVENTION

Our prior U.S. Pat. No. 5,505,728, whose contents are incorporated herein by reference, describes a novel electrosurgical electrode for ablating or shrinking palatopharynx throat tissue in a surgical procedure. This is accomplished by an electrosurgical electrode activated by electrosurgical currents that is applied by the surgeon to the patient.

There is a need in the art for devices to simplify the treatment of benign and malignant lesions of the upper aerodigestive tract. These include, among others, lesions, laryngomalacia,-cysts, laryngocele, hemangioma, stenosis, nodules, polyps, tumors, etc.

Laser have been used for such purposes in a minimally invasive surgery (MIS) procedure but has disadvantages, which include, but are not limited to: the radiation can be dangerously reflected by shiny metallic surfaces, requiring the use of non-reflective laryngo-pharyngoscopes made of special plastic which are expensive instead of the standard stainless steel laryngo-pharyngoscopes, and limiting the use of reflecting instruments; laser beam scatter may cause skin burns, fire or the generation of toxic products; problems may arise if the laser beam impinges on the endotracheal tube; safety measures are necessary such as warning lights, safety glasses, and laser safety courses are required.

SUMMARY OF THE INVENTION

An object of the invention is an improved microlarynx electrosurgical probe for treating tissue.

Another object of the invention is an improved microlarynx electrosurgical probe for treating tissue that can use a standard operating room laryngo-pharyngoscope.

Still another object of the invention is an improved microlarynx electrosurgical probe for treating tissue that avoids the use of laser radiation.

In accordance with a feature of the invention, a microlarynx electrosurgical probe comprises an elongated shaft configured such that it can be fitted down a standard operating room laryngo-pharyngoscope and allows the surgeon to conduct the procedure with improved visualization of the surgical site.

In a preferred embodiment, the elongated probe comprises at its proximal end a bare shank for fitting into a standard electrosurgical handpiece or its equivalent, and at its distal end an offset section leading to the active electrode, which may be, for example, a conventional ball, wire, needle, or loop. By "proximal" is meant the end closest to the handpiece, and by "distal" is meant the end furthest from the handpiece.

The construction of the invention will provide the same important benefits not only for MIS of lesions of the upper aerodigestive tract but also for other MIS arthroscopic procedures where the novel electrode configuration may be of importance, as well as for general electrosurgical procedures where the volumetric reduction of tissue or ablation of tissue is desirable.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals designating the same or similar elements.

BRIEF DESCRIPTION OF THE DRAWINGS

In the drawings:

FIG. 1 is a schematic view of a microlarynx electrosurgical probe according to the invention mounted in a handle or handpiece connected to electrosurgical apparatus;

FIGS. 2, 3, and 4 are, respectively, side and perspective views of one form of microlarynx electrosurgical probe according to the invention but with different active electrodes;

DETAILED DESCRIPTION OF PREFERRED EMBODIMENTS

Figure 5:
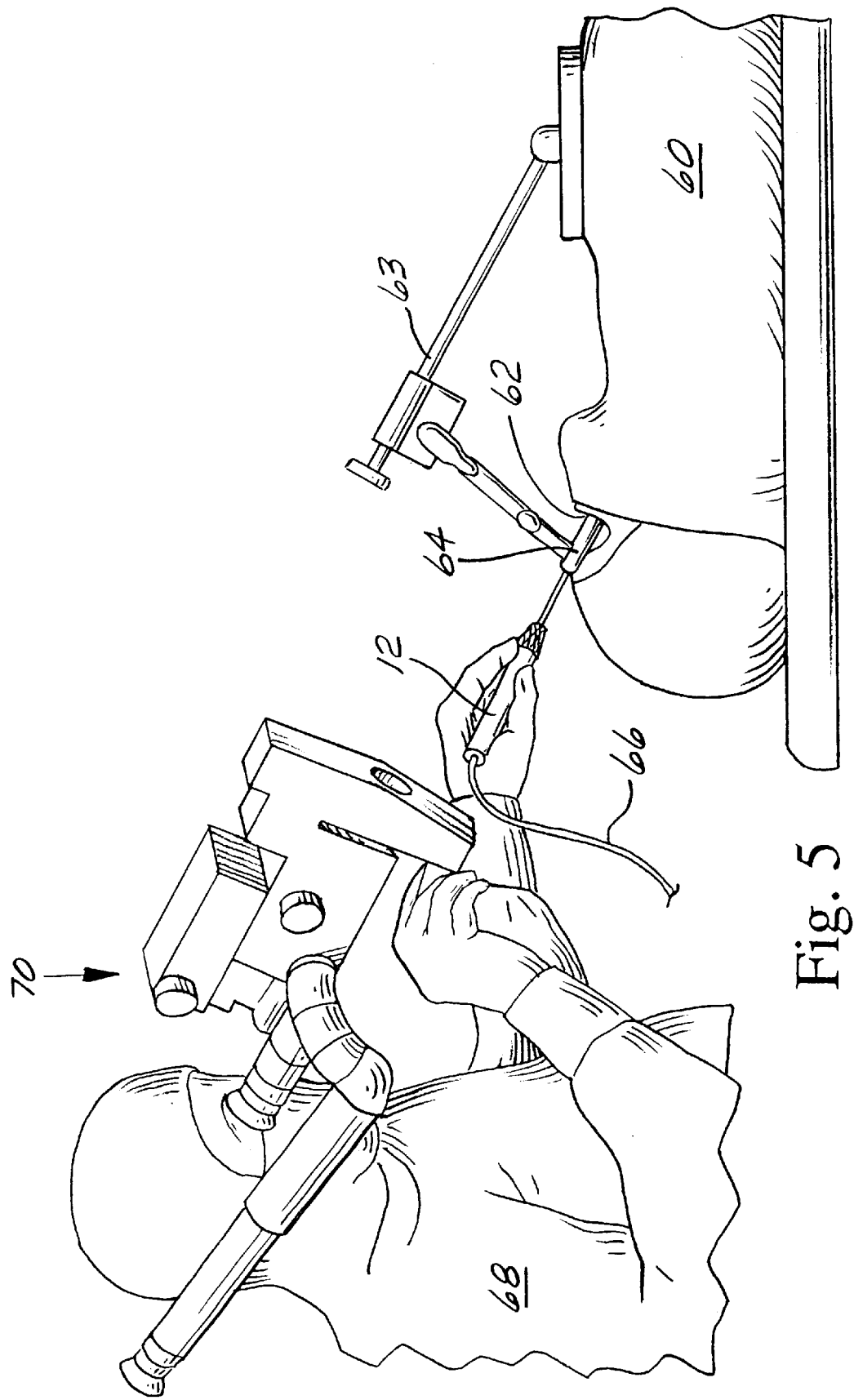
FIG. 5 is a schematic view of the probe of FIG. 2 shown in use with a patient.

The reader is directed to the referenced prior patent for a more detailed description of electrosurgical procedures and principles of operation which will assist in understanding the invention described in the present application.

In the present application, FIG. 1 is a generally schematic side view of one form of electrosurgical instrument 10 in accordance with the invention. It comprises a handle 12 with a conventional front end 14 adapted to receive and hold rigidly the shank end (not shown in FIG. 1) of an elongated electrode or probe 16 whose working end 18 is shown at the distal end. The handle 12 is typically electrically-insulating or if conductive covered with an electrically-insulating coating. Similarly, the entire electrode elongated shaft 20 except for the bare shank end, is also coated with an electrically-insulating coating, leaving bare the active electrode 24 at the working end 18. The shaft 20 is long enough to extend through the trocar or channel of a standard stainless steel laryngo-pharyngoscope so that its working end 18 is exposed inside the patient's throat. At the left end of the handle 12 is shown a cable 26 which contains wires for receiving unipolar electrosurgical currents from a conventional electrosurgical apparatus 28. The electrosurgical apparatus preferably is an ultra high frequency (RF) radiosurgical energy source, which operates in the range of about 3.8–4.0 MHz. Studies have shown that the 3.8–4.0 MHz frequency range is the preferred RF energy to incise and coagulate tissue because tissue thermal necrosis is minimal and, when interfaced with the electrosurgical electrode of the invention, provides excellent cutting and hemostasis especially for throat procedures. An example of suitable electrosurgical apparatus is the Model SURGITRON Dual-Frequency electrosurgical unit manufactured by and available from Ellman International, Inc. of Hewlett, N.Y.

FIGS. 2–4 illustrate three embodiments of the invention which differ only in the shape of the active electrode end. In FIG. 2 the active end is a needle or pointed wire 30. In FIG. 3 the active end is a ball 32. In FIG. 3 the active end is a loop 24, also as shown in FIG. 1.

The shape or configuration of the electrode 16 is significant. As will be observed, the shank 36 at the left or proximal end is bare and extends into a first electrically-insulated section 38—which is about 1 inch long, referenced 72, preferably about 0.75–1.25 inches long—that extends at an angle 40 of about 45°, preferably about 40–50°, with respect to the longitudinal or long axis 42 of the adjacent second electrically-insulated section 44,—which is about 8.75 inches long, referenced 74 preferably about 8–9.25 inches long—. The second section 44 terminates in a thinner third section 46—which is about 0.25 inches long, referenced 80, preferably about 0.1–0.33 inches long—, axially aligned with the axis 42, which leads into a fourth section 48—which is about 0.125 inches long, referenced 82, preferably about 0.1–0.3 inches long—that is offset at an angle 50 of about 155°, referenced 50, preferably about 145–165° but angles in the opposite direction from that of the first section 38. The whole electrode is in the same plane, that of the drawing. So, where the first section 38 extends downward from the axis 42, then the fourth section 48 extends upward away from the axis 42. After a short distance, the fourth section 48 leads into a fifth section 52—which is about 0.125 inches long, referenced 84, preferably about 0.1–0.3 inches long—which extends approximately parallel to the axis 42 and finally leads into the active electrode end 24, 30, 32. The third 46, fourth 48, and fifth 52 sections may all remain bare or may be covered if desired, since the ablation action occurs at the active electrode. The overall length, measured parallel to the axis 42 from the beginning or proximal end of the first section 38 to the distal end of the second section 44 is about 9.5 inches or 240 mm, which can vary about 10% in length. The significance of this configuration will be easier to understand from FIG. 5 which illustrates a typical use.

A patient 60, with his mouth 62 open, lies on a table or sits in a chair. The superstructure 63 is used to support a standard laryngo-pharyngoscope 64 which includes a scope and light whose electrical cord 66 is shown. The surgeon 68 is peering through a microscope 70 through which he or she can view the surgical site at the larynx of the patient. His left hand holds the instrument of FIG. 1 by the handle 12. The cable 26 and electrosurgical apparatus 28 are not shown in this view. The fourth electrode section 44 extends down through a channel (not shown) in the laryngo-pharyngoscope 64 with the active end exposed inside the throat of the patient and available for ablation or coagulation. The surgeon can thus manipulate the handle 12 and thus the active electrode end 24 as desired. The offset fourth section 48 increases the visibility of the active end to the surgeon who is using the scope to view the surgical site and the active electrode while conducting the procedure. The bent first section 38 allows the surgeon to hold the instrument 10 in an approximately horizontal position that he or she is accustomed to with other MIS instruments yet be capable of manipulating the active working end as needed. The overall length allows sufficient tolerance for moving the probe electrode longitudinally as needed for the procedure.

In this description, by "axial" is meant parallel to the long axis 42 of the electrode (horizontal in FIGS. 2–4). By "lateral" is meant transverse to the long axis 42. "Offset" is intended to include lateral directions as well as acute angles with respect to the long axis 42.

Once the surgeon has positioned the working end 18 of the instrument with respect to the tissue to be operated on, he or she then activates the electrosurgical apparatus 28 causing a discharge of unipolar currents between a ground plate (not shown) and the bare electrode 24, 30, 32 capable of causing excision or ablation or shrinkage of tissue or cauterization of a blood vessel in the usual way. As with the embodiments of the prior patent, the insulating coatings on the electrode 16 will prevent accidental touching of patient tissue by the electrode sides, so that the unipolar discharge is localized to the region surrounding the working end 24, 30, 32. The operation can take place in a dry or wet field. The surgeon positions the electrodes 24, 30, 32 so as to touch or pass lightly over the tissue to be modulated as needed for the procedure being followed.

For example, a suitable metal for the electrodes is brass or stainless steel. A suitable thickness of the electrode 16 is about 0.125 inches.

The benefits of the invention include: the use of a standard operating room (OR) laryngo-pharyngoscopes; no laser beam scatter can cause skin burns, fire or the generation of toxic products; the surgeon need not be concerned about a laser beam hitting an endotracheal tube which may ignite and possibly threaten a patient's life; special laser safety measures are unnecessary such as warning lights, safety glasses, and safety courses; clinically, the thermal alteration from radio frequency energy is less than that of laser energy; radiosurgery with the RF microlaryngeal probe of the invention minimizes thermal damage and penetration is negligible with radio frequency energy.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A microlarynx electrosurgical probe for treating tissue, comprising:
    (a) an elongated member having a major longitudinal axis and having a proximal first end and a distal second end comprising an active electrode,
    (b) said distal end comprising a bare active electrosurgical electrode,
    (c) said elongated member being constructed so as to allow the passage of electrosurgical currents between its proximal and distal ends,
    (d) the probe comprising, starting from the proximal end, a relatively short bare shank section, a much longer axially-extending electrically-insulating section, and a shorter section at the distal end leading to the active electrode and extending parallel to the longitudinal axis,
    (e) said section at the distal end including an offset portion with respect to the longitudinal axis,
    (f) the shank section of the probe adjacent to the first end is angled in one direction with respect to the longitudinal axis, and the offset portion is angled in direction opposite to the one direction with respect to the longitudinal axis,
    (g) wherein electrosurgical currents applied to the proximal end when an electrosurgical voltage is applied thereto will reach and activate the active end.

2. The electrosurgical probe as claimed in claim 1 wherein the offset portion is offset at an angle between about 145–165° to the axis, and the shank section is offset at an angle between about 40–50° to the longitudinal axis.

3. A microlarynx electrosurgical probe for treating tissue, comprising:
    (a) an elongated member having a major longitudinal axis and having a proximal first end and a distal second end comprising an active electrode,
    (b) said distal end comprising a bare active electrosurgical electrode,
    (c) said elongated member being constructed so as to allow the passage of electrosurgical currents between its proximal and distal ends, (d) the probe comprising, starting from the proximal end, a bare shank, a first electrically-insulating section, a second electrically-insulating section, a third section, a fourth section, and a fifth section leading to the active electrode, (e) said distal end including an offset section adjacent and leading to the active electrode, (f) the section of the probe adjacent to the first end is angled in one direction with respect to the longitudinal axis, and the offset section is angled in a direction opposite to the one direction with respect to the longitudinal axis, (g) the angled probe section that is adjacent to the first end comprises the bare shank and the first electrically-insulating section, (h) the second, third, and fifth sections extending parallel to the axis, (i) the fourth section being the offset section, (j) wherein electrosurgical currents applied to the proximal end when an electrosurgical voltage is applied thereto will reach and activate the active end.

4. The electrosurgical probe as claimed in claim 3 wherein the fourth section is offset at an angle between about 145–165° to the axis.

5. A microlarynx electrosurgical probe for treating tissue, comprising:

(a) an elongated member having a major longitudinal axis and having a proximal first end and a distal second end comprising an active electrode, (b) said distal end comprising a bare active electrosurgical electrode, (c) said elongated member being constructed so as to allow the passage of electrosurgical currents between its proximal and distal ends, (d) the probe comprising, starting from the proximal end, a bare shank, a first electrically-insulating section, a second electrically-insulating section, a third section, a fourth section, and a fifth section leading to the active electrode, (e) said distal end including an offset section adjacent and leading to the active electrode, (f) the section of the probe adjacent to the first end is angled in one direction with respect to the longitudinal axis, and the offset section is angled in a direction opposite to the one direction with respect to the longitudinal axis, (g) the angled probe section that is adjacent to the first end comprises the bare shank and the first electrically-insulating section, (h) the second, third, and fifth sections extending parallel to the axis, (i) the overall axial length of the first and second sections being about 240 mm, (j) wherein electrosurgical currents applied to the proximal end when an electrosurgical voltage is applied thereto will reach and activate the active end.

6. The electrosurgical probe as claimed in claim 5, wherein the fifth section is about the same length as or shorter than the fourth section, and the fourth section is shorter than the third section.

7. The electrosurgical probe as claimed in claim 5, wherein the fifth, fourth, and third sections are bare.

8. An electrosurgical system for treating ailments or diseases of the larynx, comprising:

(a) a laryngo-pharyngoscope, (b) an electrosurgical probe for cooperating with the laryngo-pharyngoscope, (c) said electrosurgical probe comprising:

(i) a handle, (ii) an elongated member having a major longitudinal axis and having a proximal first end and a distal second end comprising an active electrode, (iii) said distal end comprising a bare active electrosurgical electrode, (iv) said elongated member being constructed so as to allow the passage of electrosurgical currents between its proximal and distal ends, (v) the probe comprising, starting from the proximal end, a relatively short bare shank section, a much longer axially-extending electrically-insulating section, and a shorter section at the distal end leading to the active electrode and including a portion extending parallel to the longitudinal axis, (vi) said section at the distal end also including a portion being offset with respect to the longitudinal axis, (vii) the shank section of the probe adjacent to the first end is angled in one direction with respect to the longitudinal axis, and the offset portion is angled in a direction opposite to the one direction with respect to the longitudinal axis, (viii) said elongated member being sized to engage the laryngo-pharyngoscope such that the handle is accessible at one end and the offset section and active electrode project beyond the laryngo-pharyngoscope at the opposite end, (ix) wherein when electrosurgical voltages are applied to the handle and from the handle to the proximal end electrosurgical currents will reach and activate the active end.

* * * * *